United States Patent
Baughman et al.

(10) Patent No.: US 11,080,377 B2
(45) Date of Patent: *Aug. 3, 2021

(54) SYSTEM AND METHOD FOR VIRTUAL WORLD BIOMETRIC ANALYTICS THROUGH THE USE OF A MULTIMODAL BIOMETRIC ANALYTIC WALLET

(71) Applicant: INTERNATIONAL BUSINESS MACHINES CORPORATION, Armonk, NY (US)

(72) Inventors: Aaron K. Baughman, Silver Spring, MD (US); Christopher J. Dawson, Arlington, VA (US); Barry M. Graham, Silver Spring, MD (US); David J. Kamalsky, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 490 days.

This patent is subject to a terminal disclaimer.

(21) Appl. No.: 15/827,727

(22) Filed: Nov. 30, 2017

(65) Prior Publication Data

US 2018/0096227 A1    Apr. 5, 2018

Related U.S. Application Data

(62) Division of application No. 12/196,695, filed on Aug. 22, 2008.

(51) Int. Cl.
*G06F 21/32* (2013.01)
*G06F 21/62* (2013.01)
(Continued)

(52) U.S. Cl.
CPC .......... *G06F 21/32* (2013.01); *G06F 21/6245* (2013.01); *G06K 9/00885* (2013.01); *G16H 50/20* (2018.01); *G06Q 50/00* (2013.01)

(58) Field of Classification Search
CPC ...... G06F 19/30; G06F 19/34; G06F 19/3418; G06N 20/00–20; A63F 13/825
(Continued)

(56) References Cited

U.S. PATENT DOCUMENTS

| 6,219,639 B1 | 4/2001 | Bakis et al. |
| 6,545,682 B1 * | 4/2003 | Ventrella ................. G06F 3/011 345/473 |

(Continued)

FOREIGN PATENT DOCUMENTS

WO    9708868    3/1997

OTHER PUBLICATIONS

Final Office Action dated Oct. 17, 2018 in related U.S. Appl. No. 12/196,695, 25 pages.
(Continued)

*Primary Examiner* — Jay Huang
(74) *Attorney, Agent, or Firm* — Daniel Yeates; Andrew M. Calderon; Roberts Calderon Safran & Cole, P.C.

(57) ABSTRACT

The invention provides a system and method for virtual world biometric analytics through the use of a multimodal biometric analytic wallet. The system includes a virtual biometric wallet comprising a pervasive repository for storing biometric data, the pervasive repository including at least one of a biometric layer, a genomic layer, a health layer, a privacy layer, and a processing layer. The virtual biometric wallet further comprises an analytic environment configured to combine the biometric data from at least one of the biometric layer, the genomic layer, the health layer, the privacy layer, and the processing layer. The virtual biometric wallet also comprises a biometric analytic interface configured to communicate the biometric data to one or more devices within a virtual universe.

15 Claims, 8 Drawing Sheets

(51) Int. Cl.
*G06K 9/00* (2006.01)
*G16H 50/20* (2018.01)
*G06Q 50/00* (2012.01)

(58) Field of Classification Search
USPC .............................................. 600/300; 705/2
See application file for complete search history.

(56) References Cited

U.S. PATENT DOCUMENTS

| | | | |
|---|---|---|---|
| 6,945,870 B2 | 9/2005 | Gatto et al. | |
| 6,970,582 B2 | 11/2005 | Langley | |
| 7,013,365 B2 | 3/2006 | Arnouse | |
| 7,013,385 B2 | 3/2006 | Abbondanzio et al. | |
| 7,120,607 B2 | 10/2006 | Bolle et al. | |
| 7,310,042 B2 | 12/2007 | Seifert | |
| 7,360,689 B2 | 4/2008 | Beenau et al. | |
| 7,487,089 B2 | 2/2009 | Mozer | |
| 7,579,148 B2 | 8/2009 | Wohlgemuth et al. | |
| 7,894,849 B2 | 2/2011 | Kass et al. | |
| 7,941,324 B1 | 5/2011 | Sholtis | |
| 7,941,664 B2* | 5/2011 | Wheeler | G06Q 20/4014 713/170 |
| 2002/0032583 A1* | 3/2002 | Joao | G06Q 50/24 705/2 |
| 2002/0095389 A1* | 7/2002 | Gaines | G06Q 20/3674 705/67 |
| 2002/0112171 A1* | 8/2002 | Ginter | G06Q 20/085 713/185 |
| 2004/0019570 A1* | 1/2004 | Bolle | G06Q 20/3821 705/64 |
| 2004/0138864 A1* | 7/2004 | Kurzweil | G09B 23/28 703/11 |
| 2006/0104485 A1* | 5/2006 | Miller, Jr. | G06K 9/00885 382/115 |
| 2006/0136332 A1* | 6/2006 | Ziegler | G06F 21/36 705/39 |
| 2006/0265136 A1* | 11/2006 | Kouchi | G06F 19/3481 702/19 |
| 2006/0271791 A1 | 11/2006 | Novack et al. | |
| 2006/0293925 A1 | 12/2006 | Flom | |
| 2007/0047770 A1 | 3/2007 | Swope et al. | |
| 2007/0186106 A1* | 8/2007 | Ting | H04L 63/0815 713/168 |
| 2007/0198435 A1* | 8/2007 | Siegal | G06Q 20/382 705/67 |
| 2007/0294431 A1* | 12/2007 | Adelman | H04L 51/12 709/245 |
| 2008/0014566 A1* | 1/2008 | Chapman | G16H 70/60 434/262 |
| 2008/0015418 A1* | 1/2008 | Jarrell | G09B 5/00 600/300 |
| 2008/0067242 A1 | 3/2008 | Bonalle et al. | |
| 2008/0071545 A1 | 3/2008 | Novack et al. | |
| 2008/0104415 A1 | 5/2008 | Palti-Wasserman et al. | |
| 2008/0147590 A1* | 6/2008 | Bechtel | G06F 19/324 706/59 |
| 2008/0148059 A1 | 6/2008 | Shapiro | |
| 2008/0177576 A1 | 7/2008 | Jennings et al. | |
| 2008/0222706 A1 | 9/2008 | Renaud et al. | |
| 2008/0286796 A1 | 11/2008 | Grupe et al. | |
| 2008/0318673 A1* | 12/2008 | Rofougaran | A63F 13/213 463/29 |
| 2009/0029769 A1* | 1/2009 | Muller | A63F 13/816 463/31 |
| 2009/0030768 A1* | 1/2009 | Ginter | G06Q 20/04 705/39 |
| 2009/0064302 A1 | 3/2009 | Colella | |
| 2009/0228952 A1 | 9/2009 | Gillig et al. | |
| 2009/0300525 A1* | 12/2009 | Jolliff | H04L 67/306 715/764 |
| 2009/0309891 A1* | 12/2009 | Karkanias | A63F 13/10 345/581 |
| 2010/0046806 A1* | 2/2010 | Baughman | G06F 21/316 382/115 |
| 2010/0049674 A1* | 2/2010 | Zohar | G06K 9/6267 706/12 |
| 2010/0279888 A1 | 11/2010 | Park et al. | |

OTHER PUBLICATIONS

Wingfield, Nick, "Will Masses Embrace Apple's $199 Handset?", Jun. 10, 2008.
Fawaz A. Alsulaiman et al., "A Noval 3D Graphical Password Schema", 2006 IEEE Conference on Virtual Environments,Human-Computer Interfaces and Measurement Systems, pp. 125-128, Jul. 10-12, 2006.
Franziska Wolf et al., "Multimedia Content Representation Classification and Security", Article entitled "Study of Applicability of Virtual Users in Evaluating Multimodal Biometrics", Lecture notes on Computer Science, vol. 4105, Sep. 11-13, 2006, pp. 554-561.
M. Rejman-Greene, "Biometrics—Real Identities for a Virtual World", BT Technology Journal, 2001, vol. 19, No. 3 pp. 115-121.
Amit Mhatre et al., "Biometric Technology for Human Identificatin II", Article entitled "Efficient Search and Retrieval in !Biometric Databases", Proceedings of the SPIE, v SPIE-5779, pp. 265-273, Mar. 28-29, 2005.
Arun Ross, "Information fusion in biometrics", Pattern Recognition Letters 24 (2003) 2115-2125.
Anonymous, "Evolutionary Facial Feature Selection", GECCO '08, Jul. 12-16, 2008.
"Biometrics Foundation Documents", pp. 1-164, URL: http://www.biometricscatalog.org/NSTCSubcommittee, Date unknown.
Robert J. Collins, "Studies in Artificial Evolution", pp. 1-170, 1992.
Office Action dated Mar. 28, 2018, in related U.S. Appl. No. 12/196,695, 7 pages.
Office Action dated Oct. 15, 2019 in related U.S. Appl. No. 12/196,695 , 30 pages.
Notice of Allowance dated Feb. 3, 2020 in related U.S. Appl. No. 12/196,695, 10 pages.
Office Action dated Feb. 12, 2020 in related U.S. Appl. No. 15/827,840, 19 pages.
Office Action dated Feb. 13, 2020 in related U.S. Appl. No. 15/827,817, 18 pages.
Final Office Action dated Aug. 3, 2020 in related U.S. Appl. No. 15/827,840, 22 pages.
Final Office Action dated Aug. 3, 2020 in related U.S. Appl. No. 15/827,817, 19 pages.
Office Action dated Apr. 14, 2021 in related U.S. Appl. No. 15/827,817 22 pages.
Office Action dated May 3, 2021 in related U.S. Appl. No. 15/827,840, 24 pages.

* cited by examiner

SYSTEM AND METHOD FOR VIRTUAL WORLD BIOMETRIC ANALYTICS THROUGH THE USE OF A MULTIMODAL BIOMETRIC ANALYTIC WALLET

FIELD OF THE INVENTION

The invention generally relates to a system and method for combining biometric data and, in particular, to a system and method for virtual world biometric analytics through the use of a multimodal biometric analytic wallet.

BACKGROUND

A virtual universe (VU) is an interactive simulated environment accessed by multiple users through an online interface. Users inhabit and interact in the VU via avatars, which are a user's representation of himself or herself. These representations can be in the form of a three-dimensional model, a two-dimensional icon, a text construct, a user screen name, etc. Although there are many different types of VUs, there are several features many VUs generally have in common. These features include, for example, Shared Space: the VU allows many users to participate at once;
Graphical User Interface: the VU depicts space visually, ranging in style from 2D "cartoon" imagery to more immersive 3D environments;
Immediacy: interaction takes place in real time;
Interactivity: the VU allows users to alter, develop, build, or submit customized content;
Persistence: the VU's existence continues regardless of whether individual users are logged in; and
Socialization/Community: the VU allows and encourages the formation of social groups such as teams, guilds, clubs, cliques, housemates, neighborhoods, etc.

When interacting in VUs it is often difficult for a user to accurately represent himself or herself in the VU via an avatar. Moreover, it is even more difficult for a user to continuously update his or her avatar to represent the user's ever changing physical and/or behavioral characteristics. This lack of similarity between the user and his or her avatar detracts from the user's virtual experience.

In addition to detracting from the user's virtual experience, the inability of the user to accurately represent himself or herself via an avatar makes it difficult for others to verify and/or authenticate the user. Moreover, even when an avatar does accurately resemble his or her owner, the resemblance may not provide enough verification for business transactions, meetings, etc., that may occur within a VU.

SUMMARY

In a first aspect of the invention, a system includes a virtual biometric wallet comprising a pervasive repository for storing biometric data, the pervasive repository including at least one of a biometric layer, a genomic layer, a health layer, a privacy layer, and a processing layer. The virtual biometric wallet further comprises an analytic environment configured to combine the biometric data from at least one of the biometric layer, the genomic layer, the health layer, the privacy layer, and the processing layer. The virtual biometric wallet also comprises a biometric analytic interface configured to communicate the biometric data to one or more devices within a virtual universe.

In another aspect of the invention, a computer implemented method for applying biometrics in a virtual universe comprises ascertaining physiological, behavioral, and cognitive biometric data from a user in the real world; transferring the biometric data to a virtual biometric wallet; and applying the biometric data to an avatar of the user.

In another aspect of the invention, a computer program product comprising a computer usable storage medium having readable program code embodied in the storage medium is provided. The computer program product includes at least one component operable to: ascertain biometric data; link multiple types of the biometric data together using one or more analytic algorithms; transfer the biometric data to a virtual construct; and apply the biometric data to a virtual representation of a user using the virtual construct.

In yet another aspect of the invention, a method for verifying virtual users, comprises providing a computer infrastructure being operable to: ascertain characteristics and behavioral traits about a real world user; link one or more of the real world user characteristics and the behavioral traits together; apply the characteristics and behavioral traits to the virtual user; and authenticate the virtual user based on the characteristics and the behavioral traits of the real world user.

BRIEF DESCRIPTION OF THE SEVERAL VIEWS OF THE DRAWINGS

The present invention is described in the detailed description which follows, in reference to the noted plurality of drawings by way of non-limiting examples of exemplary embodiments of the present invention.

DETAILED DESCRIPTION

Figure 1:
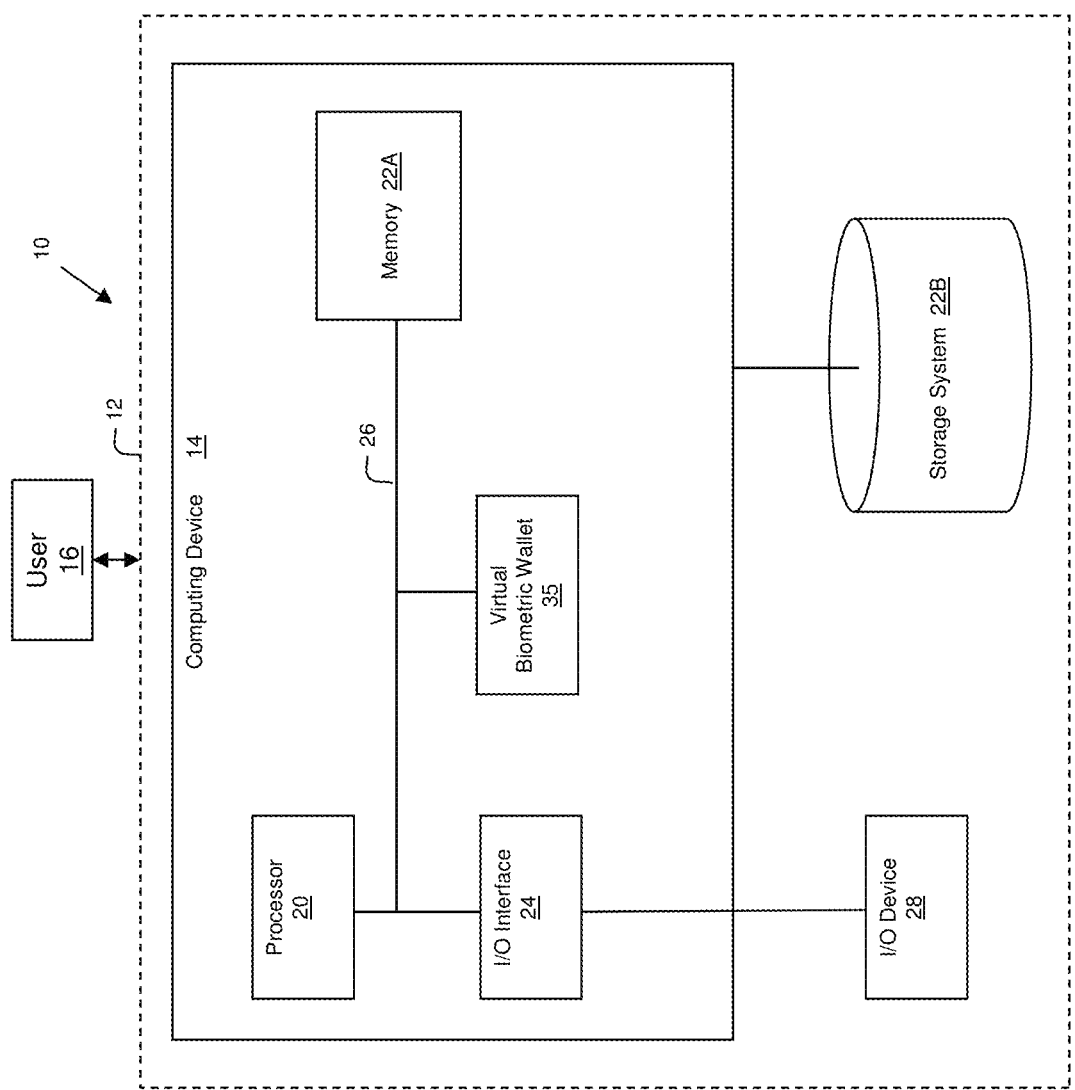
FIG. 1 shows an illustrative environment for implementing the steps in accordance with the invention.

The invention is directed to a system and method for combining biometric data and, in particular, to a system and method for virtual world biometric analytics through the use of a multimodal virtual biometric analytic wallet ("virtual biometric wallet). More specifically, the invention utilizes biometric technologies to provide identification and verification in VUs as well as to provide users with a mechanism to more accurately represent himself or herself in the VU. Any number of biometric technologies may be utilized by the invention to uniquely recognize the user based upon one or more of his or her intrinsic physical, cognitive, or behavioral traits. Exemplary biometrics may include fingerprints, facial patterns, iris patterns, deoxyribonucleic acid (DNA), voice recognition, etc.

There are multiple systems that may be used to acquire biometric data from real world users for authentication purposes. For example, unimodal biometric systems may be used to acquire a single biometric characteristic, such as a fingerprint, for authentication. However, unimodal systems are unable to combine other biometric analytic data for user authentication.

Multimodal biometric systems may also be used to acquire biometric data from real world users for authentication purposes. Unlike unimodal systems, multimodal biometric systems attempt to integrate traditional and behavioral biometric characteristics for user authentication. Existing multimodal biometric systems include statically defined biometric acquisition points, fusion policies, and computational algorithms for user authentication. However, existing multimodal systems do not combine multimodal information and do not include other types of information such as the human genome, health data, and family history.

Manual health data systems may also be used to acquire biometric data from one or more devices. Exemplary devices may include magnetic resonance imaging (MRI) and functional MRI (fMRI) as well as devices such as a stethoscope. However, manual health data systems fail to provide an amorphous service oriented architecture to combine multi-modal information. Moreover, there is no way to use the acquired health data for verification or authentication in a VU.

The present invention allows biometric data to be acquired from a real world user via any one or more of the above noted devices or from any number of additional devices known to those of skill in the art. Once acquired, the biometric data can be sent to a virtual biometric wallet comprising a pervasive repository, an analytic environment, and one or more biometric analytic interfaces.

The virtual biometric wallet is configured to allow disparate biometric information to be stored on a pervasive storage device or repository that can be used to authenticate users and avatars, in the VU. The pervasive repository may store a plurality of different types of biometric information. For example, the pervasive repository may include a storage layer for a user's biometric data, genomic data, and health data. The biometric data may include physiological, behavioral, and/or cognitive biometric information. The genomic data may include DNA information about the user and the health layer may include, e.g., family information and medical history.

In embodiments, the pervasive repository may also include a privacy layer which provides mechanisms to protect biometric data from being acquired from remote sensing. The pervasive repository may also include a processing layer configured to provide continuous biometric analytic processing and data mining for health analysis, behavioral predictions, physiological monitoring, and environment cues. These layers make it possible for the pervasive repository to support disparate biometric analytic acquisition with the potential for multi-modal rollup.

The virtual biometric wallet is further configured to include an analytic environment configured to act on data to combine health, genomic, physiological, behavioral, and cognitive distributed analysis. In embodiments, the analytic environment may comprise a continuous machine-learning environment and an application environment. The learning environment may obtain exemplar data from multiple sources and use the exemplar data to train one or more algorithms in order to ascertain appropriate weights and heuristics for the algorithms. These weights and heuristics may be used in the application environment to link user characteristics and behavioral traits. Embodiments may also use the analytic environment to produce health informatics.

In addition to a pervasive repository and analytic environment, the virtual biometric wallet may also comprise a biometric analytic interface, which enables the transportation and analysis of real time on-body information within the VU. In particular, the biometric analytic interface allows the information stored in the pervasive repository and combined in the analytic environment to be sensed by one or more acquisition devices within the VU. In embodiments, the acquisition devices may include remote sensors that act as service points for the virtual biometric wallet.

Accordingly, the present invention beneficially allows disparate biometric information to be stored on a pervasive storage device and used to identify and verify users and avatars in the VU. Moreover, embodiments also allow the biometric information obtained about a user to be mapped onto the user's avatar to make the avatar appear, act, sounds, etc., like the user. Beneficially, this allows the user to emulate their real world state and provides the user with a notion of presence while in the VU.

The invention also beneficially provides mechanisms for combining genomic, health and biometric data as well as deriving a user's cognitive state. This allows real world and VU environments to become aware of a user's identity and reduces the risk of virtual fraud and doppleganging, i.e., cloning.

System Environment

As will be appreciated by one skilled in the art, the present invention may be embodied as a system, method or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer-usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following:
  a portable computer diskette,
  a hard disk,
  a random access memory (RAM),
  a read-only memory (ROM),
  an erasable programmable read-only memory (EPROM or Flash memory),
  a portable compact disc read-only memory (CDROM),
  an optical storage device, and/or The computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

In the context of this document, a computer-usable or computer-readable medium may be any medium that can contain, store, communicate, propagate, or transport the program for use by or in connection with the instruction execution system, apparatus, or device. The computer usable program code may be transmitted using any appropriate transmission media via a network.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network. This may include, for example, a local area network (LAN) or a wide area network (WAN), or the connection may be made to an external computer (for example, through the Internet using an Internet Service Provider).

FIG. 1 shows an illustrative environment 10 for managing the processes in accordance with the invention. To this extent, the environment 10 includes a computer infrastructure 12 that can perform the processes described herein. In particular, the computer infrastructure 12 includes a computing device 14 that comprises a Virtual Biometric Wallet 35, which makes computing device 14 operable to acquire, process, and transmit biometric data in accordance with the invention, e.g., process described herein.

The computing device 14 also includes a processor 20, a memory 22A, an I/O interface 24, and a bus 26. The memory 22A can include local memory employed during actual execution of program code, bulk storage, and cache memories which provide temporary storage of at least some program code in order to reduce the number of times code must be retrieved from bulk storage during execution.

The computing device 14 is in further communication with the external I/O device/resource 28 and the storage system 22B. For example, the I/O device 28 can comprise any device that enables an individual to interact with the computing device 14 or any device that enables the computing device 14 to communicate with one or more other computing devices using any type of communications link. The external I/O device/resource 28 may be keyboards, displays, pointing devices, microphones, headsets, etc. The storage system 22B can include an "inventory" of sounds, modifications, etc., which may be selected by the user's avatar.

In general, the processor 20 executes computer program code, which is stored in the memory 22A and/or storage system 22B. The computer code may be representable of the functionality of the Virtual Biometric Wallet 35. While executing computer program code, the processor 20 can read and/or write data to/from memory 22A, storage system 22B, and/or I/O interface 24. The program code executes the processes of the invention. The bus 26 provides a communications link between each of the components in the computing device 14.

The computing device 14 can comprise any general purpose computing article of manufacture capable of executing computer program code installed thereon (e.g., a personal computer, server, handheld device, etc.). However, it is understood that the computing device 14 is only representative of various possible equivalent computing devices that may perform the processes described herein. To this extent, in embodiments, the functionality provided by the computing device 14 can be implemented by a computing article of manufacture that includes any combination of general and/or specific purpose hardware and/or computer program code. In each embodiment, the program code and hardware can be created using standard programming and engineering techniques, respectively.

Similarly, the server 12 is only illustrative of various types of computer infrastructures for implementing the invention. For example, in embodiments, the server 12 comprises two or more computing devices (e.g., a server cluster) that communicate over any type of communications link, such as a network, a shared memory, or the like, to perform the processes described herein. Further, while performing the processes described herein, one or more computing devices on the server 12 can communicate with one or more other computing devices external to the server 12 using any type of communications link. The communications link can comprise any combination of wired and/or wireless links; any combination of one or more types of networks (e.g., the Internet, a wide area network, a local area network, a virtual private network, etc.); and/or utilize any combination of transmission techniques and protocols.

In embodiments, the invention provides a business method that performs the steps of the invention on a subscription, advertising, and/or fee basis. That is, a service provider, such as a Solution Integrator, could offer to perform the processes described herein. In this case, the service provider can create, maintain, deploy, support, etc., a computer infrastructure that performs the process steps of the invention for one or more customers. In return, the service provider can receive payment from the customer(s) under a subscription and/or fee agreement and/or the service provider can receive payment from the sale of advertising content to one or more third parties.

Exemplary Implementation of the System

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Pervasive Repository

The virtual biometric wallet comprises a pervasive repository, which is configured to store physiological, behavioral, and cognitive traits and characteristics with health data and a subject's genome. In embodiments, one or more distributed sub-instances of the pervasive repository may be created, thereby making the pervasive repository inherently distributed. The distributed sub-instances may be created based on determined privacy policies, which may be loaded onto extensible items with biometric analytic interfaces. For example, a biometric analytic interface may include a privacy policy that designates what information another biometric analytic interface or acquisition device may obtain. The pervasive repository and/or one or more distributed sub-instances of the pervasive repository may be embodied as a storage unit 22B.

The traits, characteristics, and data in the pervasive repository may be synched to a central repository via a biometric analytic interface, as described in more detail herein. For example, as a traveling distributed database or inventory item moves in and out of range of the central repository, both may be synched. The range within which the synching occurs may be dynamically defined and may relate to a geographical virtual distance such as inches, feet, yards, meters, and/or miles, etc. Optionally, the range may relate to, e.g., the distance in which a person may be heard while shouting, talking, and/or whispering within the VU.

Figure 2:
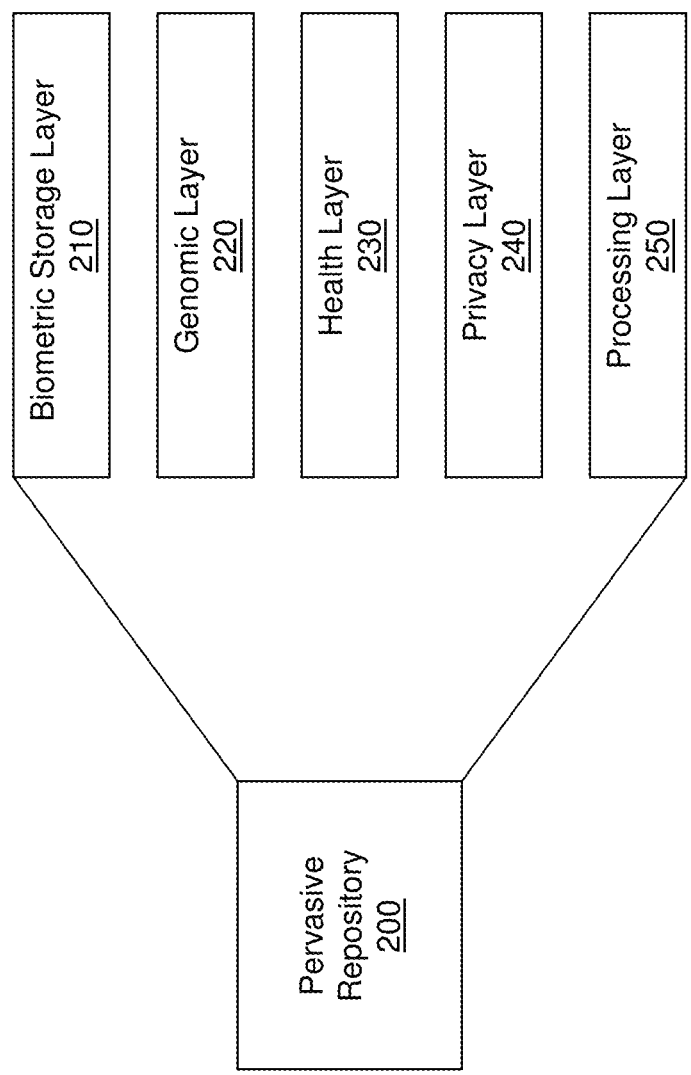
FIG. 2 shows a pervasive repository comprising five layers according to aspects of the invention.

FIG. 2 shows a pervasive repository comprising five layers in accordance with embodiments of the invention. The five layers of the pervasive repository 200 include a biometric storage layer 210, a genomic layer 220, a health layer 230, a privacy layer 240, and a processing layer 250. While five layers are disclosed herein, it should be understood by those skilled in the art that the present invention is not limited to five layers and may be expanded to include additional layers as appropriate.

Figure 3:
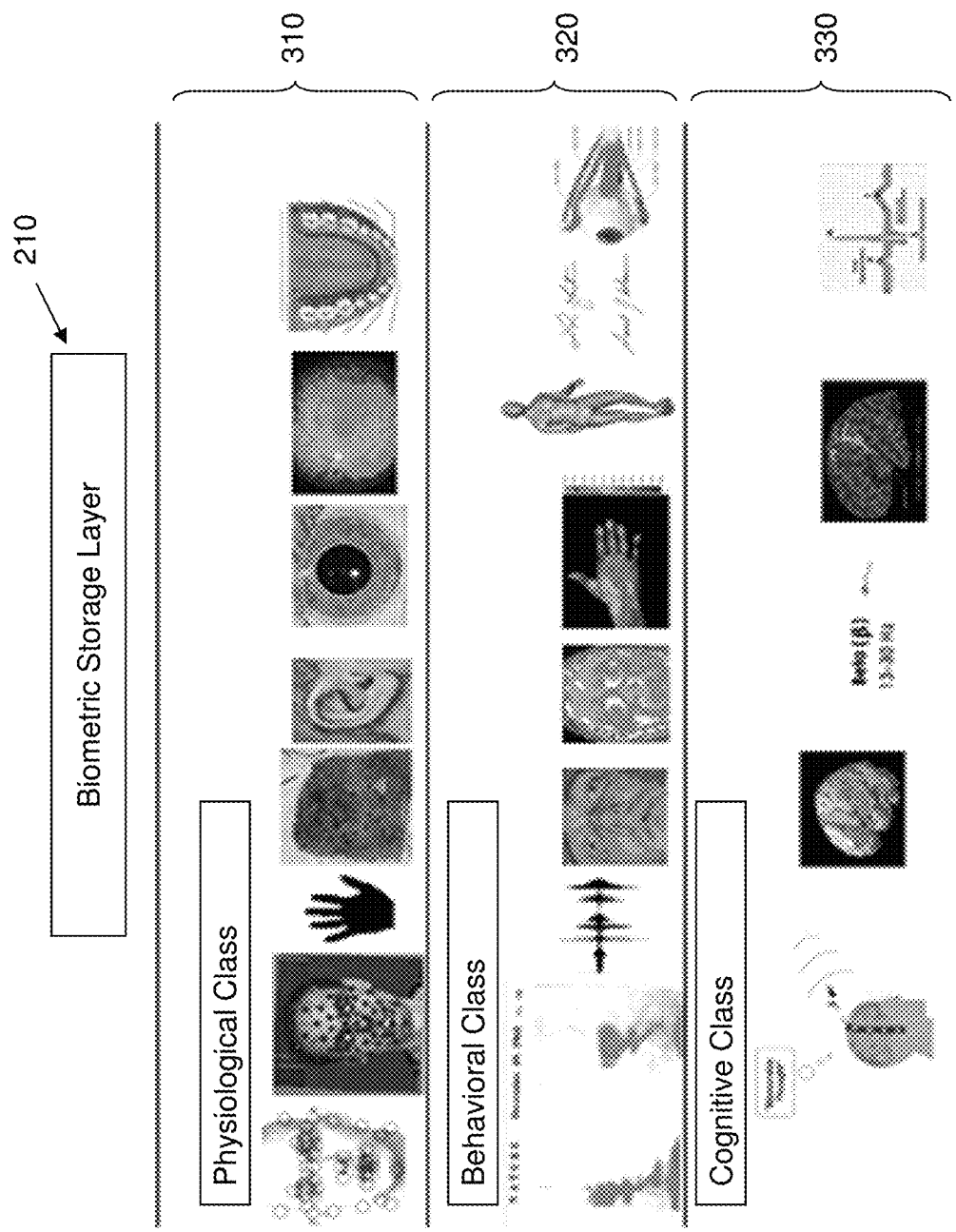
FIG. 3 shows a biometric storage layer according to aspects of the invention.

FIG. 3 shows a biometric storage layer in accordance with embodiments of the invention. The biometric storage layer 210 may be used to store information acquired from a person's body and may include trigger points for health monitoring. In embodiments, the information can be divided into three classes or layers of biometric information including physiological 310, behavioral 320, and cognitive 330 information.

The physiological layer 310 may include biometrics relating to a person's physical characteristics. These characteristics may include the person's face, hand geometry, fingers, ear/pina, iris, retina and/or teeth, etc. In embodiments, additional physiological information may also be obtained and stored in the physiological layer 310 or in a user defined field. An exemplary user defined field may be illustrated in accordance with aspects of the Federal Bureau of Investigation's Electronic Fingerprint Transmission Specification (EFTS).

The behavioral layer 320 may include biometrics relating to the person's actions and/or conduct. For example, the behavioral layer 320 may include characteristics relating to a person's voice such as vocal tract encoding and/or voice spectral information. The behavioral layer 320 may also include biometrics relating to skin luminescence, thermograms, venule/arteriole/vein/artery blood flow, signature, eye movement, and/or gait, etc.

The cognitive layer 330 may include biometrics relating to a person's thinking, learning, perception, awareness, and/or judgment. For example, the cognitive layer 330 may provide a storage mechanism for thought patterns, Purkinje fiber activations, functional magnetic resonance imaging (fMRI) under labeled movements and thoughts, limb control brain mapping, and/or electrocardiogram (ECG) recordings with respect to thought and movement, etc.

Figure 4:
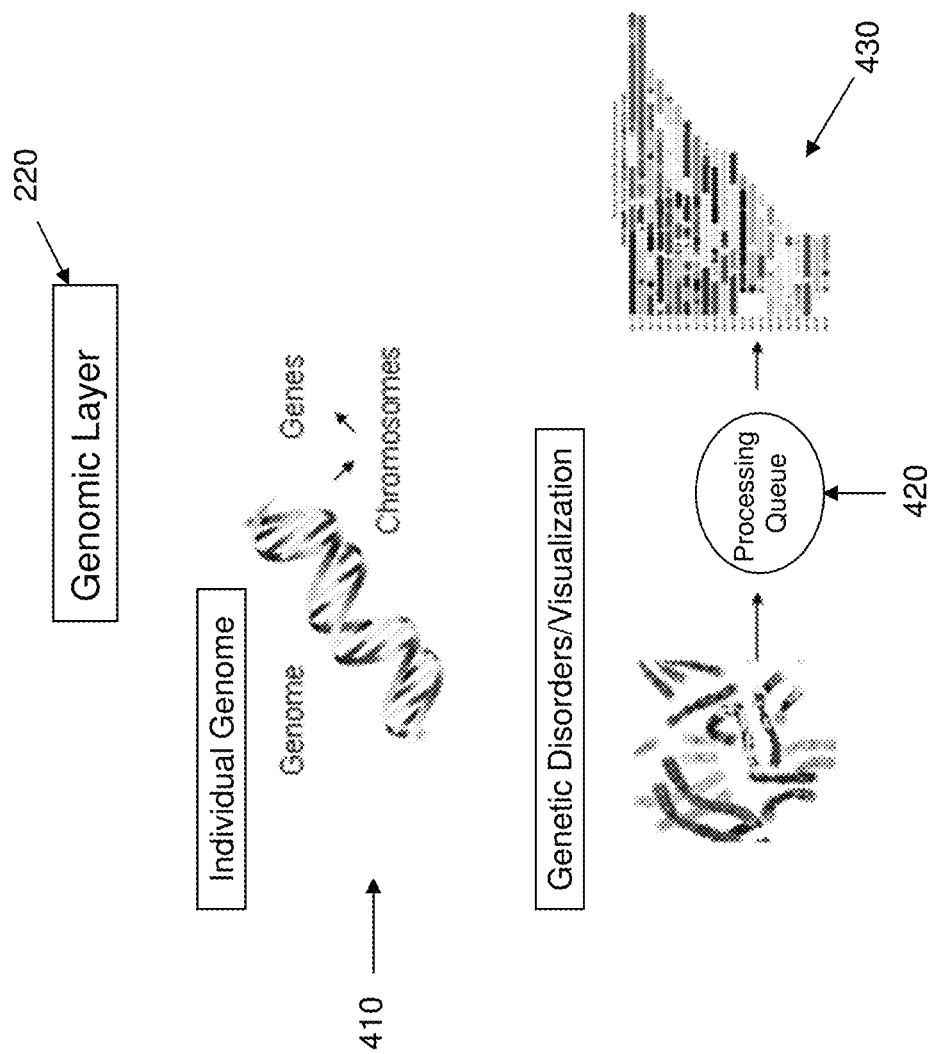
FIG. 4 shows a genomic layer according to aspects of the invention.

FIG. 4 shows a genomic layer in accordance with embodiments of the invention. The genomic layer 220 is configured to maintain a list of one or more genetic disorders. In embodiments, these genetic disorders may be synched with a distributed genetic disorder database.

In particular, the genomic layer 220 may store information about the virtual biometric wallet owner's genome 410, genes, and/or chromosomes. A genome 410 is the complete genetic sequence of an organism, which is stored on a chromosome. A chromosome consists of a DNA helix on which thousands of genes are encoded. Each gene corresponds to a unit of inheritance, which may be associated with regulatory regions, transcribed regions, and/or other functional sequence regions.

The genomic layer 220 may process the owner's genomic sequence. In embodiments, this processing may be performed using a processing queue 420, which may keep a line of patterns 430. These patterns 430 may be searched and compared with known genetic disorders to determine whether the owner has a possible genetic risks and/or disorders. The genetic disorders may be maintained by the genomic layer 220 and synched with a distributed genetic disorder database.

Thus, the genomic layer 220 stores an individual's genome 410 and processes it to determine genetic disorders. The patterns 430 from the genetic disorders may be continually or periodically searched using one or more search algorithms. If a probable match is found, the resulting nucleotide matches may be stored for data retrieval.

Figure 5:
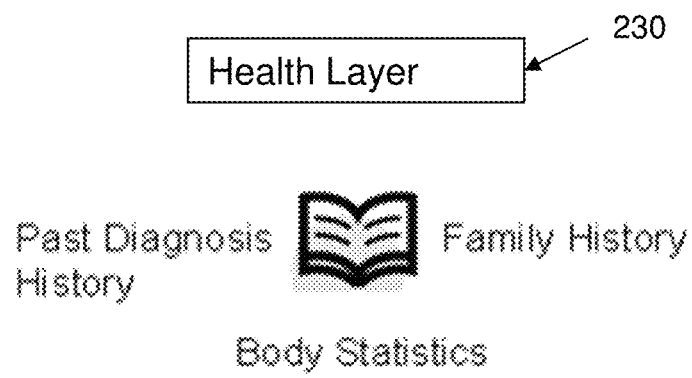
FIG. 5 shows a health layer according to aspects of the invention.

FIG. 5 shows a health layer in accordance with embodiments of the invention. The health layer 230 is configured to provide knowledge that may be correlated with the person's health state and risk factors. The health layer 230 may include the person's diagnosis history, family records, hereditary diseases, current health status, bodily statistics, and/or regional epidemiology factors. In embodiments, one or more of these factors may be used to provide predictive health monitoring and suggestions via a biometric analytic interface.

For example, the health layer 230 may maintain knowledge as to the last time the person was sick and recent symptoms the person has had. This information may be compared to the person's family records and/or the person's hereditary diseases to determine possible ailments that may be inflicting the person. The possible ailments may be acquired by a health care professional via an acquisition device and used to diagnose the person.

Figure 6:
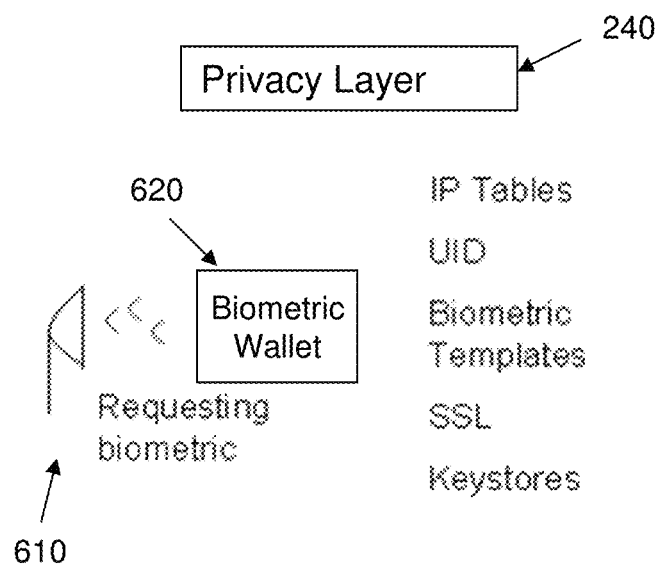
FIG. 6 shows a privacy layer according to aspects of the invention.

FIG. 6 shows a privacy layer in accordance with embodiments of the invention. The privacy layer 240 is configured to protect personal data and enable multi-layer security so that only authenticated individuals or automated systems 610 are granted access to the information stored in the user's virtual biometric wallet 620. Thus, for example, a person's hereditary diseases may only be accessible to the user and the user's physician.

A variety of methods may be used to ensure data privacy. For example, the privacy layer 240 may employ any number of cancelable biometric technologies, which perform a distortion on one or more biometric images or features before authenticating the user. The distortion may be performed using a non-invertible biometric template stored within the biometric storage layer. In embodiments, any number of variable parameters may be utilized to provide the non-invertible function.

The privacy layer 240 may include additional types of data protection. For example, the privacy layer may include keystores, which provide certificates signed by certificate authorities for a public key infrastructure (PKI). Moreover, the privacy layer 240 may use secure socket layers (SSL) and encryption capabilities to protect the user's biometric data from public interception and/or packet snooping. Additional exemplary data protections may include, e.g., internet protocol tables, user identifiers (UID), internet protocol filtering, and/or access control lists and encryption, etc.

Figure 7:
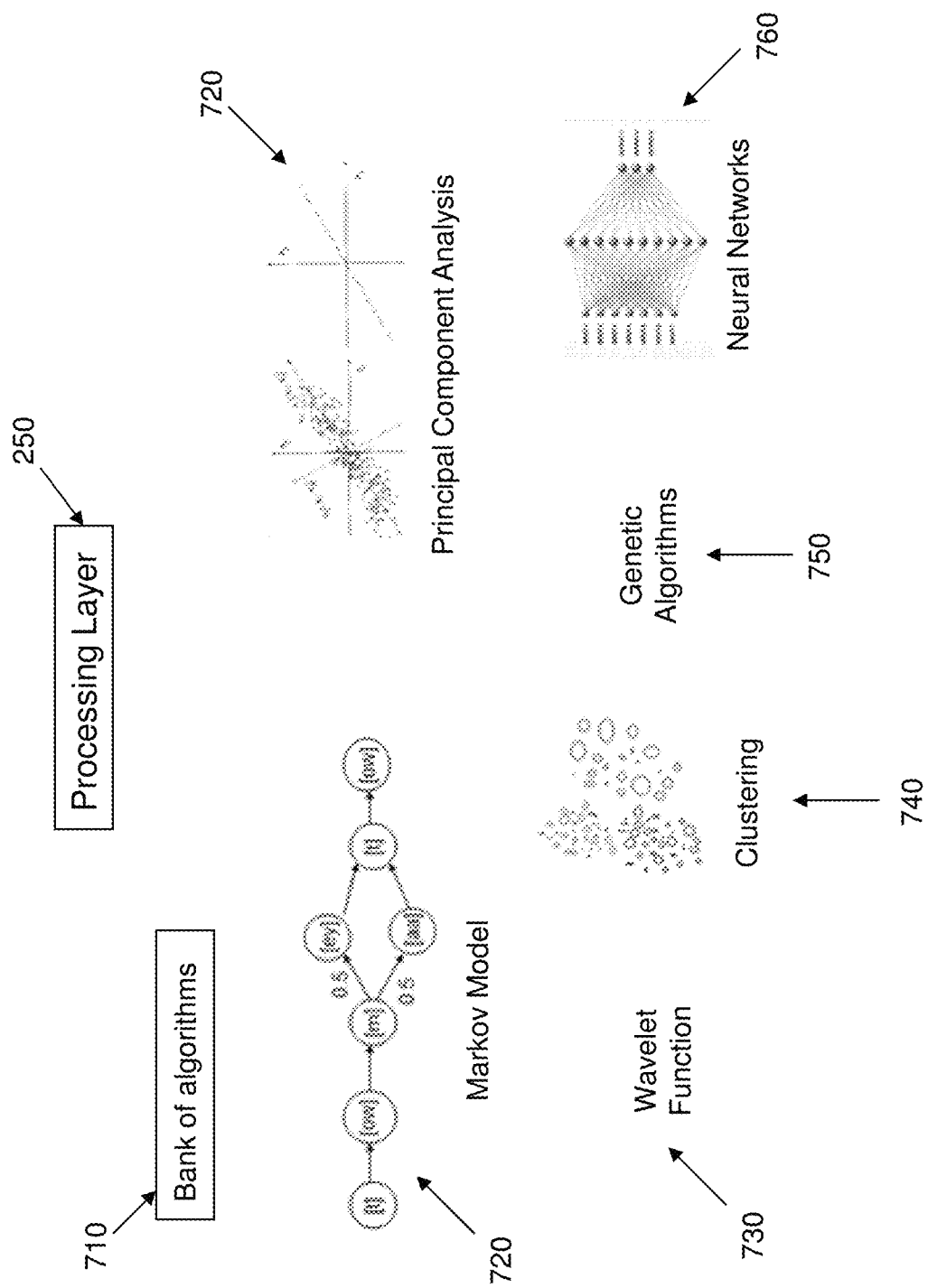
FIG. 7 shows a processing layer according to aspects of the invention.

FIG. 7 shows the processing layer in accordance with embodiments of the invention. The processing layer 250 is configured to provide continuous biometric analytic processing and data mining for health analysis, behavioral predictions, physiological monitoring, and environment cues.

In particular, the processing layer 250 performs computations and reasoning using one or more algorithms from a bank of algorithms 710. Exemplary algorithms in the bank of algorithms 710 may include, but are not limited to, Markov models, principal component analysis (PCA), clustering, genetic algorithms, wavelet functions, and neural networks. Additional algorithms known to those of skill in the art may also be included for feature extraction, pattern recognition, classification, and data mining, etc.

For example, the bank of algorithms 710 may include the Markov model 720, which uses probabilistic processes to reach future states instead of relying on past states. The exemplary Markov model illustrated in FIG. 7 represents the pronunciation of the word "tomato". In addition to the Markov model, embodiments may also include the hidden Markov model (HMM), which determines hidden parameters based on observable parameters. The HMM may be used for temporal pattern recognition of biometrics such as speech, handwriting, gesture recognition, gait, etc.

A number of algorithms may be included in the bank of algorithms 710 to decrease the dimensionality of the data. For example, a PCA 720 algorithm may be included to reduce multidimensional data into a lower dimension. Additionally, a wavelet function 730 may also be included for object recognition and image dimensionality reduction.

Clustering algorithms 740 may also be included in the bank of algorithms 710 to, e.g., decrease search space and cluster images. For example, clustering may be used to gather a number of images of a person's healthy bone and compare the images to gathered images of a broken bone. Based on the analysis, a determination may be made as to where the bone is broken and how badly the bone is broken.

The bank of algorithms 710 may also include any number of genetic algorithms 750, which may be used for bioinformatics, gene expression profiling, protein folding, etc. Additionally, the bank of algorithms 710 may include one or more neural networks 760, which comprise algorithms for understanding how biological systems work. In embodiments, the neural networks 760 may include artificial interconnected neurons that are representable of human biological neural networks.

In embodiments, the processing layer may also provide a staging processing area to provide training on biometric data and health data. The staging processing area may provide, for example, heuristic selection and machine-learning. After algorithm training, the production stage enables real time signal and data processing.

Analytic Environment

Figure 8:
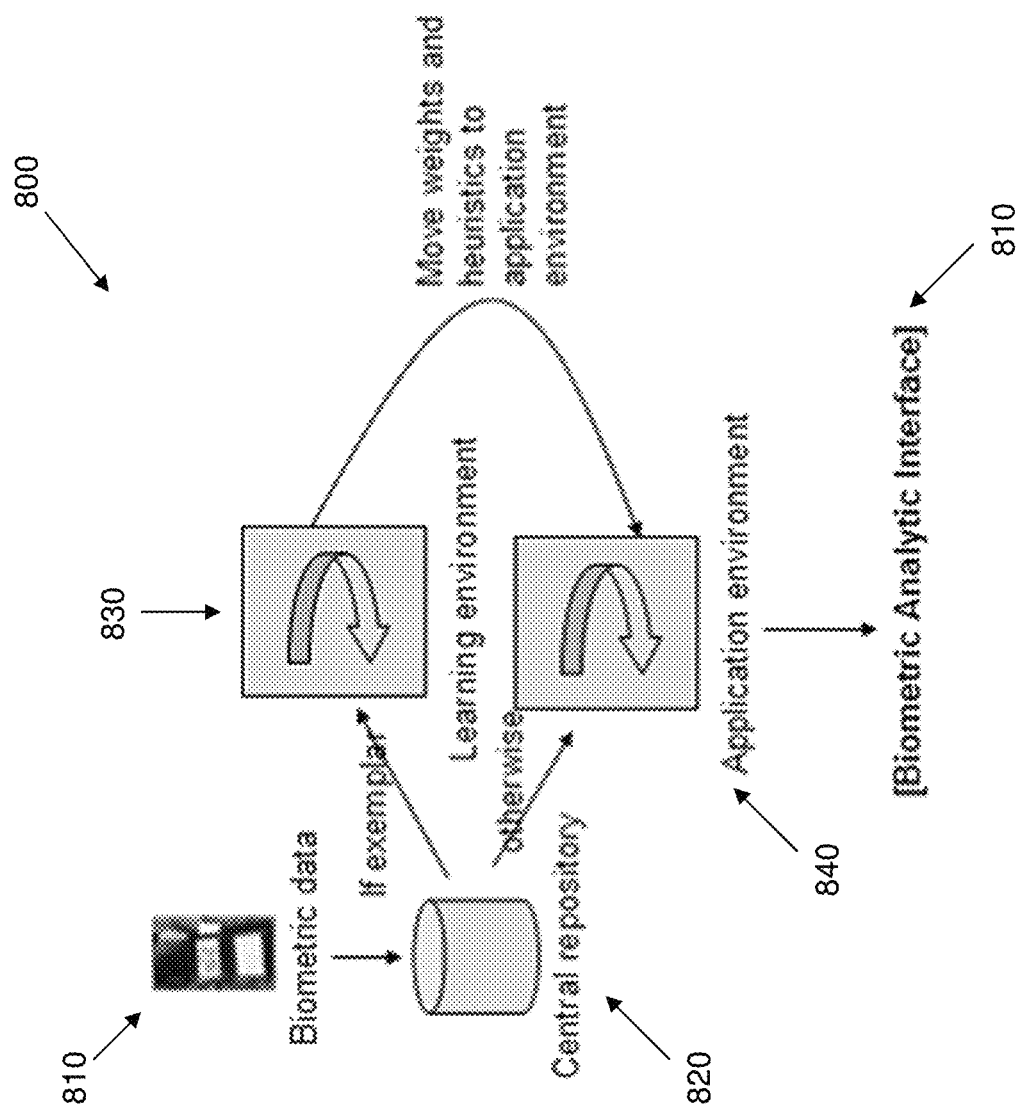
FIG. 8 shows portions of an analytic environment according to aspects of the invention.

FIG. 8 shows aspects of an analytic environment according to embodiments of the invention. The analytic environment 800, which may be part of the virtual biometric wallet, is configured to train algorithms, which may be used by the processing layer of the pervasive repository. As the distributed analytic environment 800 spreads into VUs, counter part acquisition devices may increase the amount of data to process.

The analytic environment 800 acts on biometric data to combine health, genomic, physiological, behavioral, and cognitive distributed analysis. In doing so, the analytic environment utilizes biometric data 810, which may be obtained from one or more sensors or pervasive devices that are scattered throughout the VU. The acquired data may be passed to a central repository 820 through one or more biometric analytic interfaces. The central repository 820 is configured to store biometric data obtained from a plurality of virtual biometric wallets and, in embodiments, pass the obtained biometric data to the analytic environment 800. The central repository 820 may be embodied as a storage unit 22B.

The biometric data 810 from the central repository 820 may be identified as exemplar data or non-exemplar data. Exemplar data, or training data, may be defined by the user and/or an administrator and may be sent to a continuous machine-learning environment 830 to train one or more algorithms. Once trained, the weights and/or heuristics from the continuous machine-learning environment 830 may be sent to the application environment 840. The application environment 840 may include the same algorithms that were used in the continuous machine-learning environment 840 and apply the weights and/or heuristics from the continuous machine-learning environment 840 to the incoming non-exemplar data. This allows the algorithms to be trained and applied to incoming non-exemplar data so that unimodal and/or multimodal biometric data may be combined. Once combined, the application environment 840 may send one or more of the trained algorithms to the processing layer of the pervasive repository via the biometric analytic interface.

This allows respective algorithms from the application environment to be replicated to support desired functions.

A number of classes of analytic algorithms may be used in the analytic environment 800. The exemplary classes may relate to reasoning, clustering algorithms, pattern recognition, data mining, search and/or optimization, dimensionality reduction, etc. Each of these classes may include one or more analytic algorithms, which may be applied in the continuous machine-learning environment and/or the application environment.

For example, embodiments may include a reasoning class of algorithms comprising Bayes probability, belief networks, neural networks, HMMs, Markov models, etc. Embodiments may also include a clustering class of algorithms relating to patterns, graphs, models, and/or density. Exemplary pattern algorithms may include K-means, C-means, etc. Exemplary graph algorithms may include minimum spanning trees (MST), spatial graphs, etc. Model based clustering algorithms may also be included such as, e.g., mixture models. Additional clustering algorithms, such as density based algorithms may include, e.g., kernel based models.

In embodiments, pattern recognition classes may include, e.g., neural networks, discriminative feature space (DFFS), linear discriminative analysis (LDA), HMMs, Gabor filters, state vector machines, etc. Data mining classes may include algorithms that are vector based, Boolean, probabilistic, breadth/depth, bi-directional, iterative deepening, etc. In embodiments, search/optimization classed of algorithms may include A* search trees, mini-max algorithms, search algorithms, etc. Additionally, the dimensionality reduction class may include, e.g., PCA, independent component analysis, etc. Any one or more of the analytic algorithms in these exemplary classes may be stored in a continuous machine-learning environment and/or an application environment and used to, e.g., link user characteristics and behavioral traits.

Biometric Analytic Interface

One or more algorithms, policies, and/or heuristics may be loaded onto extensible items with biometric analytic interfaces. Biometric analytic interfaces are ubiquitous interfaces configured to provide service points to acquisition devices, traveling repositories, and analytic environments. In essence, biometric analytic interfaces may be embodied as amorphous service oriented architectures. In embodiments, one or more biometric analytic interfaces may be included in the virtual biometric wallet.

Biometric analytic interfaces may be included in any number of VU items including clothing, accessories, digital and mechanical devices, as well as any other extensible item. For example, biometric analytic interfaces may be included in a number of virtual inventory items such as, e.g., cards, phones, sweaters, shoes, eye glasses, etc. The biometric analytic interfaces are configured to provide mechanisms for parallel acquisition and processing as well as to provide a mechanism to synch to a central repository. In embodiments, the type of biometric analytic interface may affect the algorithms and/or communication rules provided to the processing layer of the pervasive repository.

Figure 9:
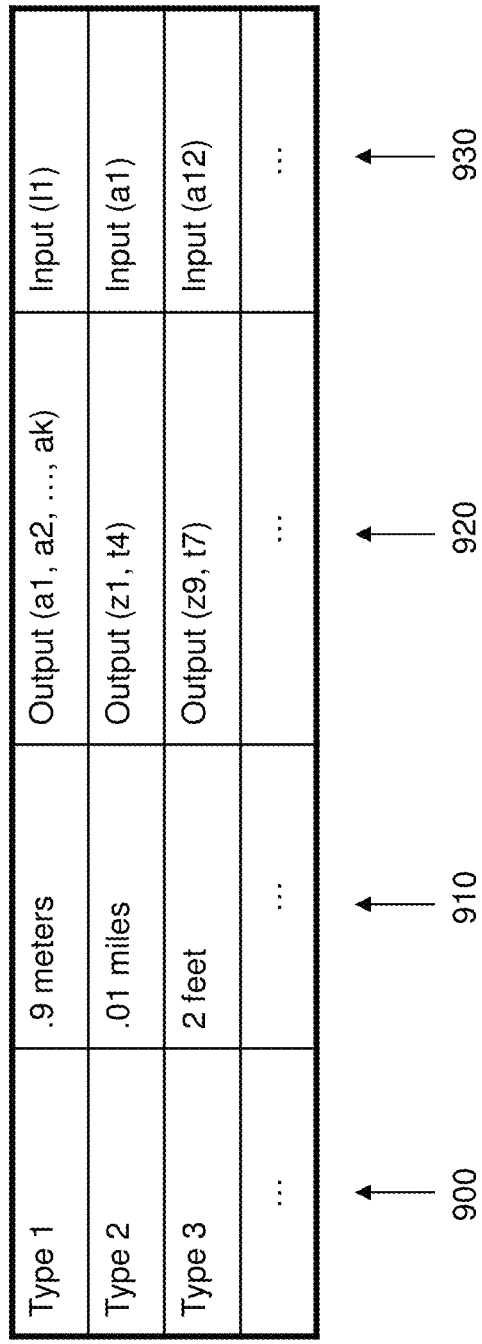
FIG. 9 shows an exemplary biometric analytic interface knowledge representation according to aspects of the invention.

FIG. 9 shows an exemplary biometric analytic interface knowledge representation in accordance with embodiments of the invention. In particular, FIG. 9 includes a biometric analytic interface type, in column 900. The type of biometric analytic interface may include, e.g., a person's watch, a virtual store kiosk, a physician, etc.

FIG. 9 also includes an activation column 910, which identifies the range the biometric analytic interface should be from an acquisition device, such as another biometric analytic interface, a central repository, etc. In embodiments, the range may be in inches, feet, yards, meters, and/or miles, etc. Optionally, the range may relate to, e.g., the distance in which a person may be heard while shouting, talking, and/or whispering within the VU. While a range is indicated in activation column 910, it should be understood by those skilled in the art that any number of mechanisms and/or events may be used to determine when and/or how frequently biometric information can be obtained from the virtual biometric wallet's biometric analytic interface.

An output column 920 and an input column 930 may also be included as part of the biometric analytic interface. The output column 920 may represent the knowledge sent from the biometric analytic interface to the acquisition device. The input column 930 may represent information that may be sent to one or more algorithms, communication rules, etc. In embodiments, the algorithms, communication rules, etc., may be based on the type of biometric analytic interface.

For example, type 1 may be representative of a virtual kiosk having a biometric analytic interface. The biometric analytic interface may acquire and process information obtained from an avatar within a 0.9 meter activation range of the virtual kiosk. The biometric analytic interface may also send information about the avatar as output. The amount and/or type of information sent as output may depend on the biometric analytic interface's privacy policy, as defined by the user. In embodiments, an input may be used to send information to one or more algorithms, communication rules, etc., which may be included in the processing layer of the pervasive repository.

Virtual Biometric Wallet

Biometric data obtained in the real world may be stored in an avatar's virtual biometric wallet. The virtual biometric wallet may be multimodal and provide a consolidation of multimodal biometric storage. In embodiments, the virtual biometric wallet may further encompass virtual identification systems, ID cards, visas, licenses, and/or voter registration, etc., in addition to the real world biometric data. This information may be used to, e.g., provide virtual advertisements and entertainment that is tailored towards each avatar's virtual biometric wallet.

Identification and verification services may be provided by the virtual biometric wallet. Additionally, in embodiments, virtual checks may be performed on the user and/or virtual biometric wallet to identify or verify that the avatar is who he or she claims to be. These verifications may be performed continuously or periodically to determine, e.g., whether the user has possession of his or her virtual biometric wallet. In embodiments, the verifications may be performed by comparing the user's incoming real world biometric data with the biometric data stored in the user's virtual biometric wallet. The verifications may also be performed, e.g., by requiring the user to periodically insert a code, password, thumbprint, and/or other personal information to verify that the user is in possession of his or her virtual biometric wallet and that the virtual biometric wallet has not been misappropriated. If the person possessing the virtual biometric wallet is not the user, the virtual biometric wallet may discontinue data collection and/or take steps to prevent unauthorized access to the data within the virtual biometric wallet. In embodiments, a similar check may be performed on one or more of the acquisition devices.

Information in the virtual biometric wallet may be obtained from the biometric analytic interface using one or more VU acquisition devices, which may include one or more biometric analytic interfaces. In embodiments the biometric analytic interface may include a privacy policy that designates what information the acquisition device may obtain. Thus, a user may limit automated and/or manual access to biometric, genomic, and/or health data, etc.

In embodiments, a user may be allowed to designate information or types of information that cannot be acquired unless permission is given to the acquisition device and/or the entity or thing associated with the acquisition device. Beneficially, this allows the user to control who has access to the user's information. In embodiments, the user may change permissions when the user comes into contact with an acquisition device. Moreover, in embodiments, the virtual biometric wallet may track what acquisition devices have requested information from the user, allow the user to access the tracked information, and/or permit the user to change permissions for one or more of the acquisition devices based on the tracked information.

For example, real world biometric information may be continuously obtained about a user and continuously or periodically transferred to the user's virtual biometric wallet. The user may carry this information in the user's virtual biometric wallet and give permission to the user's virtual physician to acquire specific types of information from the user's virtual biometric wallet. Thus, the virtual physician may be allowed to acquire private medical biometric information from the user such as health data, genetic information, etc. This information may be obtained via an acquisition device and used for diagnosis purposes. In embodiments, the physician may also be allowed to monitor one or more biometric factors via the virtual biometric wallet.

In addition to storing health data and genetic information, the virtual biometric wallet may also provide continuous data analysis on health, biometric, and genomic information. The information in the virtual biometric wallet may be mapped onto a user's avatar to emulate a user's attitude, physical condition, and/or mood. For example, derived knowledge such as thought patterns can be acquired in the real world from an electroencephalogram (EEG) and contrasted to a baseline image. The results of this comparison may provide insights into mood and the veracity of thoughts. Brain structure change may also be derivable through pattern recognition. These types of cognitive biometrics, which are stored within a virtual biometric wallet, can be used to reflect the user's current moods and/or conditions through the user's avatar. Moreover, the moods and/or conditions may also be used to help doctors with the administration of anti-depressants, selective serotonin reuptake inhibitors (SSRI), and deep brain stimulation. As information and knowledge is gained from the user's real world state, medical informatics may be continuously or periodically synched back to the pervasive repository for use within the VU.

Embodiments may map the user's real world cognitive, behavioral, and/or physical traits onto the user's avatar. For example, physiological, behavioral, and/or cognitive biometric information may be obtained and transferred to the user's virtual biometric wallet, wherein the biometric information may be used to deduce that the user is angry in the real world. In embodiments, this deduction may be used to make the user's avatar appear angry in the VU, thereby augmenting the avatar's emotions based on the user's real world emotions.

A user's real world behavior traits may also be mapped onto the user's avatar to provide a more realistic virtual experience. For example, a person's real world behavioral traits such as gait, voice, tics, and signature may be stored in the user's virtual biometric wallet for avatar identification and verification. Real world cognitive traits such as thoughts and intelligence may also be translated to the virtual biometric wallet to make the user's avatar more representative of the user and/or for avatar identification and verification purposes.

In addition to behavioral and cognitive traits, embodiments may translate real physiological traits such as fingerprint, face, palm, pina shape, hand knife, iris, retina, DNA and signature to the virtual biometric wallet. This allows the user's avatar to have, e.g., the same fingerprints, face, and/or iris, etc., as the real world user and heightens the user's virtual experience. Additionally, this information also aids in identification and verification of the user via the user's avatar.

Examples of Use

The virtual biometric wallet may facilitate security in VUs. For example, a VU may control virtual access to conferences, secure business transaction processing, and/or areas having confidential information. Before being admitted to one or more of these secured locations, the user's avatar may be asked to provide virtual biometrics, which are representative of the user's real world biometrics. Thus, a virtual user may be verified by his or her real world biometric information as portrayed by the user's avatar.

In addition to providing security in business transactions, conferences, processing, etc., the virtual biometric wallet may also provide authority figures and scientists with tools to solve crimes. For example, forensic scientists and/or authority figures may utilize virtual DNA, hair samples, and other virtual biometric traits to identify criminals and fight virtual crime. This may be performed, e.g., by comparing information from an avatar's virtual biometric wallet to real world or VU information that is known about a criminal.

In embodiments, authorities, governments, etc., may use the virtual biometric wallet for surveillance and/or pervasive computing. For example, authorities may compare information from the virtual biometric wallet to criminal and/or terrorist watch lists. Additionally, real time tracking and/or anchor alerts may use the virtual biometric wallet to obtain information about criminals.

In embodiments, the virtual biometric wallet may also be used by employer's to screen employees. For example, the virtual biometric wallet may be used to readily portray cognitive, behavioral and/or physiological biometrics via a user's avatar. Moreover, in embodiments, the user may also be able to gather biographical data on employees and prospective employees. This information may be used to determine whether the employee is wanted for a crime, has substance abuse problems, etc. Understandably, the employer's access to information in the virtual biometric wallet may be limited by the user.

Embodiments of the invention may allow biometric information from the user's virtual biometric wallet to be used to diagnosis the user in the VU via the user's avatar. For example, the user's avatar may visit a virtual clinic and speak with a virtual physician. The virtual physician can also examine the avatar based on the real world biometric traits that have been mapped onto the avatar via the virtual biometric wallet. This information, together with information the virtual physician derives from the user's virtual biometric wallet, may be used to diagnose and treat the user.

In addition to diagnosing a user via the user's avatar, embodiments may also perform simulated treatments on the user's avatar. For example, a user having an ailment such as cancer may see a virtual physician for treatment. The virtual physician may recommend one or more treatments, which may be administered to the user's avatar before being administered to the real world user. This allows the user to go through a personalized trial wherein the results of the treatment may be analyzed and/or adjusted before the treatment is administered to the user. In embodiments, a plurality of treatments may be administered at once by cloning the avatar and applying one or more of the treatments to each of the cloned avatars to determine what treatment or combination of treatments would be most effective for the user.

As described above the present invention provides numerous advantages that can be understood by those of skill in the art such as, e.g., increasing the usefulness of raw data and analysis results. Additionally, the biometric analytic interfaces enable pervasive devices to read, transmit and store algorithms, data and results. By fusing health, genomic, physiological, behavioral and cognitive data, accurate systemic states can be represented by avatars in the VU. This beneficially allows human to computer interaction to be blended by increasing human presence within virtual worlds and by sensing and processing prosthesis within the real world.

While the invention has been described in terms of embodiments, those skilled in the art will recognize that the invention can be practiced with modifications and in the spirit and scope of the appended claims. Additionally, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated. Accordingly, while the invention has been described in terms of embodiments, those of skill in the art will recognize that the invention can be practiced with modifications and in the spirit and scope of the appended claims.

What is claimed is:

1. A method for deploying an application for verifying virtual users, comprising:
   providing a computer infrastructure being operable to:
   ascertain real world user characteristics and behavioral traits about a real world user;
   ascertain genetic data comprising DNA information, family health information, and medical history of the real world user;
   ascertain a genomic sequence of the genetic data of the real world user;
   process the genomic sequence of the real world user to generate a line of patterns for the genomic sequence of the real world user;
   compare the line of patterns for the genomic sequence of the real world user to a plurality of genetic risks and genetic disorders;
   determine whether the real world user has at least one of the genetic risks and genetic disorders based on the comparing of the line of patterns;
   link one or more of the real world user characteristics and the behavioral traits together;
   apply the real world user characteristics, the genetic data comprising the DNA information, the family health information, and the medical history of the real world user, the determined at least one of the genetic risks and genetic disorders and behavioral traits to a virtual user; and
   authenticate the virtual user through a privacy layer based on the real world user characteristics, the genetic data comprising the DNA information, the family health information, and the medical history of the real world user, the behavioral traits of the real world user, and the at least one of the genetic risks and genetic disorders.

2. The method of claim 1, wherein the real world user characteristics and the behavioral traits include at least one of physiological biometric data, behavioral biometric data, and cognitive biometric data.

3. The method of claim 1, wherein the computer infrastructure is at least one of supported, deployed, maintained, and created by a service provider.

4. The method of claim 1, wherein the behavioral traits include at least one of gait, voice, tics, and signature.

5. The method of claim 1, wherein the real world user characteristics include at least one of physical characteristics and behavioral characteristics.

6. The method of claim 5, wherein the physical characteristics include at least one of a person's face, hand geometry, fingers, ear, iris, retina and teeth.

7. The method of claim 5, wherein the behavioral characteristics include at least one of vocal tract encoding and voice spectral information.

8. The method of claim 1, further comprising the computer infrastructure being operable to train one or more algorithms in order to ascertain appropriate weights and heuristics for the one or more algorithms.

9. The method of claim 8, wherein the computer infrastructure is operable to utilize the weights and heuristics for the one or more algorithms to link the one or more of the real world user characteristics and the behavioral traits together.

10. The method of claim 1, wherein the virtual user is an avatar in a virtual universe.

11. The method of claim 10, further comprising providing a virtual diagnosis of the avatar in the virtual universe.

12. The method of claim 11, further comprising simulating treatment of the avatar in the virtual universe using the virtual diagnosis.

13. The method of claim 1, further comprising storing any corresponding nucleotides in response to a determination that the user has at least one of the genetic risks and genetic disorders.

14. The method of claim 13, further comprising diagnosing the real world user based on the corresponding nucleotides.

15. The method of claim 14, further comprising simulating treatment of the virtual user based on the diagnosed real world user.

\* \* \* \* \*